United States Defensive Publication [19] (H) [11] T104,301

Palmere [43] Jun. 5, 1984

[54] PROCESS FOR PRODUCING PYRETHROID INTERMEDIATES

[76] Inventor: Raymond M. Palmere, 17 Morris Rd., West Orange, N.J. 07052

[21] Appl. No.: 541,403

[22] Filed: Oct. 13, 1983

[51] Int. Cl.[3] ..... C07C 87/28

[52] U.S. Cl. ..... 564/337

[57] ABSTRACT

Disclosed is a process for the preparation of an optionally substituted N,N-2-trimethyl-[1,1'-biphenyl]-3-methanamine, Compound II, by rearrangement of a N,N,N-trimethyl-]1,1'-biphenyl]-2-methanaminium compound, Compound I. Compound I is treated with at least one equivalent of sodium or lithium methylsulfinyl carbanion in the presence of dimethylsulfoxide at a temperature in the range of 0° to 70° C. to give Compound II. The process is conveniently conducted by adding lithium hydride or sodium hydride to excess dimethylsulfoxide to produce a solution of the lithium or sodium methylsulfinyl carbanion, then adding Compound I to the solution thus formed.

Compound II is a useful intermediate for the preparation of insecticidal pyrethroid esters of formula IV. Compound II may be converted into ester IV by treatment with ethyl chloroformate or cyanogen bromide to give intermediate III, followed by reaction with an alkali metal or ammonium salt of the desired pyrethroid acid.

In the following formulas, R and $R^1$ are independently halogen, alkyl, fluoromethyl, alkoxy, or fluoroalkoxy, m is 0 to 3, n is 0 to 5, Y is a chloride, bromide, iodide, or hydroxide ion, X is chlorine or bromine, and $R^2CO_2$ is a pyrethroid acid moiety.

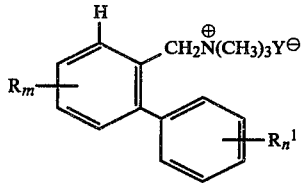

I

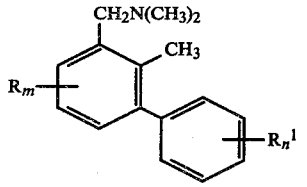

II

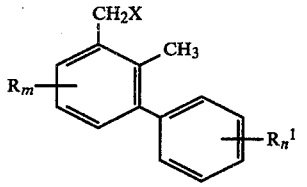

III

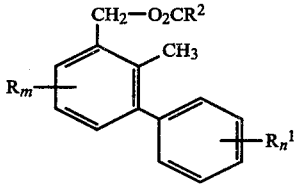

IV

5 Claims, No Sheets Drawing,

12 Pages Specification

The file of this unexamined application may be inspected and copies thereof may be purchased (849 O.G. 1221, Apr. 9, 1968).